(12) United States Patent
Mihelich et al.

(10) Patent No.: US 6,608,099 B1
(45) Date of Patent: Aug. 19, 2003

(54) INDOLE SPLA$_2$ INHIBITORS

(75) Inventors: Edward David Mihelich, Carmel, IN (US); Michael LeRoy Phillips, Indianapolis, IN (US); Alan M Warshawsky, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/762,070

(22) PCT Filed: Aug. 2, 1999

(86) PCT No.: PCT/US99/17460

§ 371 (c)(1),
(2), (4) Date: Jan. 30, 2001

(87) PCT Pub. No.: WO00/07591

PCT Pub. Date: Feb. 17, 2000

Related U.S. Application Data

(60) Provisional application No. 60/095,109, filed on Aug. 3, 1998.

(51) Int. Cl.$^7$ ..................... A61K 31/404; C07D 209/14
(52) U.S. Cl. .................... 514/419; 514/235.2; 514/323; 514/397; 544/144; 546/208; 548/312.1; 548/493
(58) Field of Search ............................. 514/235.2, 323, 514/397, 419; 544/144; 546/208; 548/312.1, 493

(56) References Cited

U.S. PATENT DOCUMENTS

| | | |
|---|---|---|
| 5,578,634 A | 11/1996 | Bach et al. |
| 5,641,800 A | 6/1997 | Bach et al. ................. 514/415 |
| 5,654,326 A | 8/1997 | Bach et al. |
| 5,684,034 A | 11/1997 | Bach et al. |

*Primary Examiner*—Deborah C. Lambkin
*Assistant Examiner*—Sonya Wright
(74) *Attorney, Agent, or Firm*—Roger S. Benjamin

(57) ABSTRACT

A class of novel acylsulfonamide substituted indole compounds is disclosed together with the use of such compounds for inhibiting sPLA$_2$ mediated release of fatty acids for treatment of inflammatory diseases.

6 Claims, No Drawings

INDOLE SPLA₂ INHIBITORS

This application claims the benefit of U.S. Provisional Application 60/095,109 filed Aug. 3, 1998.

FIELD OF THE INVENTION

This invention relates to novel indole compounds useful for inflammatory diseases.

BACKGROUND OF THE INVENTION

The structure and physical properties of human non-pancreatic secretory phospholipase $A_2$ (hereinafter called, "$sPLA_2$") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

Indole type sPLA2 inhibitors having gyloxylamide, acetamide and hydrazide substituents are described in U.S. Pat. Nos. 5,654,326; 5,684,034; and 5,578,634 respectively.

It is believed that $sPLA_2$ is a rate limiting enzyme in the arachidonic acid cascade which hydrolyzes membrane phospholipids. Thus, it is important to develop compounds which inhibit $sPLA_2$ mediated release of fatty acids (e.g., arachidonic acid). Such compounds would be of value in general treatment of conditions induced and/or maintained by overproduction of $sPLA_2$; such as sepsis or rheumatoid arthritis.

It is desirable to develop new compounds and treatments for $sPLA_2$ induced diseases.

SUMMARY OF THE INVENTION

This invention is a class of novel indole compounds to inhibit mammalian $sPLA_2$ mediated release of fatty acids.

This invention is also a novel class of indole compounds having potent and selective effectiveness as inhibitors of mammalian $sPLA_2$.

This invention is also a indole compound useful in the treatment of Inflammatory Diseases.

This invention is also a pharmaceutical composition containing novel indoles of the invention.

This invention is also a method of preventing and treating Inflammatory Diseases in mammals by administration of a therapeutically effective amount of the indole of the invention.

This invention is also the indole compounds of the invention or compositions comprising the compounds of the invention as active ingredient for use as a medicament in the treatment of Inflammatory Diseases.

Definitions

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit $sPLA_2$ mediated release of fatty acid and to thereby inhibit or prevent the arachidonic acid cascade and its deleterious products.

The term, "indole nucleus" refers to a nucleus (having numbered positions) with the structural formula (X):

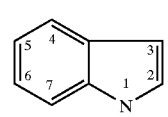

(X)

The indole compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "halo" means fluoro, chloro, bromo, or iodo.

The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl,morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a):

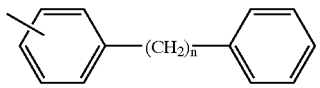

(a)

where n is a number from 1 to 8.

The term, "non-interfering substituent", refers to radicals suitable for substitution at positions 4,5,6 and/or 7 of the indole nucleus and on other nucleus substituents (as hereinafter described for Formula I), and radicals suitable for substitution on the heterocyclic radical and carbocyclic radical as defined above. Illustrative non-interfering radicals are $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —($CH_2$)$_n$—O—($C_1$–$C_8$ alkyl), benzyloxy, phenoxy, phenylthio, —(CONHSO2R),—CHO, amino, amidino, bromo, carbamyl, carboxyl, carbalkoxy, —($CH_2$)$_n$—$CO_2$H, chloro, cyano, cyanoguanidinyl, fluoro, guanidino, hydrazide, hydrazino, hydrazido, hydroxy, hydroxyamino, iodo, nitro, phosphono, —$SO_3$H, thioacetal, thiocarbonyl, and $C_1$–$C_8$ carbonyl; where R is $C_1$–$C_8$ alkyl and n is from 1 to 8.

The term "substituted group" is an organic group substituted with one or more non-interfering substituents.

The term, "(acylsulfonamide group)" is a group represented by the formula:

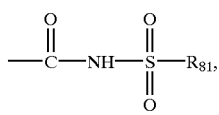

where $R_{81}$ is —$CF_3$ or an organic substituent consisting of carbon and hydrogen with or without oxygen, nitrogen, sulfur, halogen or other elements.

The term "indole acylsulfonamide compound" is synonymous with the term "indole compound."

The words, "linker" refer to a divalent linking group symbolized as, —($L_a$)—, which has the function of joining the 4 or 5 position of the indole nucleus to an acylsulfonamide group in the general relationship:

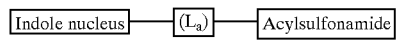

The words, "linker length", refer to the number of atoms (excluding hydrogen) in the shortest chain of the linking group —($L_a$)— that connects the 4 or 5 position of the indole nucleus with the acylsulfonamide group. The presence of a carbocyclic ring in —($L_a$)— counts as the number of atoms approximately equivalent to the calculated diameter of the carbocyclic ring. Thus, a benzene or cyclohexane ring in the linker counts as 2 atoms in calculating the length of —($L_a$)—. Illustrative linker groups are;

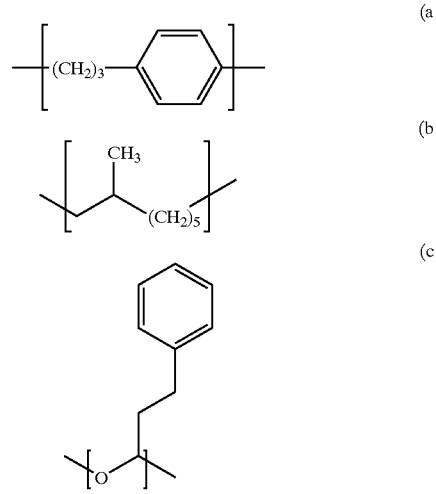

wherein, groups (a), (b), and (c) have linker lengths of 5, 7, and 2, respectively.

The term, "amine", includes primary, secondary and tertiary amines.

The terms, "mammal" and "mammalian" include human.

The term, "alkylene chain of 1 or 2 carbon atoms" refers to the divalent radicals, —$CH_2$—$CH_2$— and —$CH_2$—.

The term, "group containing 1 to 4 non-hydrogen atoms" refers to relatively small groups which form substituents at the 2 position of the indole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —$CF_3$, —Cl, —Br, —$NO_2$, —CN, —$SO_3$; and (ii) groups having hydrogen atoms which contain less than 4 non-hydrogen atoms such as —$H_3$, —$C_2H_5$, and —CH═$CH_2$.

The term "spiro [5.5] undecanyl" refers to the group represented by the formula;

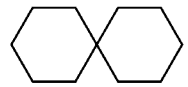

The term "organic substituent" is a monovalent radical consisting of carbon and hydrogen with or without oxygen, nitrogen, sulfur, halogen or other element. Illustrative organic substituents are —$CH_3$, —$C_2H_5$, —$CH_2OCH_3$, and —$CH_2SCH_3$.

The indole Compounds of the Invention:

The compounds of the invention have the general formula (I) or a pharmaceutically acceptable salt or solvate thereof;

$$\text{(I)}$$

wherein;

each X is independently oxygen or sulfur;

$R_1$ is selected from groups (a), (b) and (c) wherein;
 (a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical, or
 (b) is a member of (a) substituted with one or more independently selected non-interfering substituents; or
 (c) is the group —($L_1$)—$R_{11}$; where, —($L_1$)— is a divalent linking group of 1 to 8 atoms and where $R_{11}$ is a group selected from (a) or (b);

$R_2$ is hydrogen, or a group containing 1 to 4 non-hydrogen atoms plus any required hydrogen atoms;

$R_3$ is —($L_3$)—Z, where —($L_3$)— is a divalent linker group selected from a bond or a divalent group selected from:

—CH$_2$—, —O—, —S—, —N(H)— or —C(=O)— and Z is selected from acetamide, thioacetamide, glyoxylamide, thioglyoxylamide, hydrazide or thiohydrazide groups represented by the formulae, where $R_{31}$ and $R_{32}$ are independently selected from hydrogen, $C_1$–$C_8$ alkyl, $C_1$–$C_8$ haloalkyl, and $C_3$–$C_4$ cycloalkyl, and X is oxygen or sulfur;

$R_4$ and $R_5$ are independently selected from hydrogen, a non-interfering subtituent, or the group, —($L_a$)— (acylulfonamide group); wherein —($L_a$)—, is a linker having a linker length of 1 to 8, provided, that at least one of $R_4$ and $R_5$ must be the group, —($L_a$)— (acylsulfonamide group); and the (acylsulfonamide group) is represented by the formula;

$$-\overset{O}{\underset{}{C}}-NH-\overset{O}{\underset{O}{S}}-R_{81},$$

where $R_{81}$ is selected from the group consisting of $C_1$–$C_8$ alkyl, $C_1$–$C_8$ alkoxy, $C_1$–$C_8$ alkylthio, $C_1$–$C_8$ alkylamino, $C_1$–$C_8$ haloalkyl, $C_1$–$C_{14}$ aralkyl, $C_1$–$C_{14}$ alkylaryl, aryl, thioaryl, $C_3$–$C_{14}$ carbocyclic radical, $C_3$–$C_{14}$ heterocyclic radical.

$R_6$ and $R_7$ are selected from hydrogen, non-interfering subtituent, carbocyclic radical, carbocyclic radical, subtituent with non-interfering substituent(s), heterocyclic radical, and heterocyclic radical substituent with non-interfering substituent(s).

Preferred Subgroups of Compound of Formula (I):

I. Preferred $R_1$ Substituents:

A preferred subclass of compounds of formula (I) wherein for $R_1$ the divalent linking group —($L_1$)— are those corresponding to the formulae (VIIa), (VIIb), (VIIc), (VIId), (VIIe), and (VIIf):

$$-\underset{H_2}{C}- \quad \text{(VIIa)}$$

$$-O- \quad \text{(VIIb)}$$

$$-S- \quad \text{(VIIc)}$$

$$-\underset{H}{N}- \quad \text{or} \quad \text{(VIId)}$$

$$-\underset{\underset{O}{\|}}{C}- \quad \text{or} \quad \text{(VIIe)}$$

$$\left(\!\!\begin{array}{c} R_{10} \\ | \\ Q_1\!-\!C \\ | \\ R_{10} \end{array}\!\!\right) \quad \text{(VIIf)}$$

where $Q_1$ is a bond or any of the divalent group (VIIa), (VIIb), (VIIc), (VIId), (VIIe), and (VIIf) and each $R_{10}$ is independently hydrogen, $C_{1-8}$ alkyl, $C_{1-8}$ haloalkyl or $C_{1-8}$ alkoxy.

Particularly preferred as the linking group —($L_1$)— of $R_1$ is an alkylene chain of 1 or 2 carbon atoms, namely, —(CH$_2$)— or —(CH$_2$—CH$_2$)—.

The preferred group for $R_{11}$ is a subtituted or unsubstituted group selected from the group consisting of $C_5$–$C_{14}$ cycoalkyl, $C_5$–$C_{14}$ cycloalkenyl, phenyl, naphthyl, norbornanyl, bicycloheptadienyl, tolulyl, xylenyl, indenyl, stilbenyl, terphenylyl, diphenylethylenyl, phenyl-cyclohexenyl, acenaphthylene, and anthracenyl, biphenyl, bibenzylyl, and related bibenzylyl homologues represented by the formula (a);

$$\text{(a)}$$

where n is a number from 1 to 8.

Particularly preferred are compounds wherein for $R_1$ the combined group —($L_1$)—$R_{11}$ is selected from the group consisting of $$-(CH_2)_{1-2}- \text{phenyl}-(R_{12})_t \quad \text{or}$$

-continued

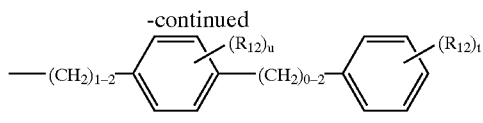

where $R_{12}$ is a radical independently selected from halo, $C_1-C_8$ alkyl, $C_1-C_8$ alkoxy, —S—($C_1-C_8$ alkyl), —O—($C_1-C_8$ alkyl) and $C_1-C_8$ haloalkyl where t is a number from 0 to 5 and u is a number from 0 to 4.

II. Preferred $R_2$ substituents:

$R_2$ is preferably selected from the group consisting of hydrogen, $C_1-C_4$ alkyl, $C_2-C_4$ alkenyl, —O—($C_1-C_3$ alkyl), —S—($C_1-C_3$ alkyl), —$C_1-C_4$ cycloalkyl —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

III. Preferred $R_3$ Substituents:

A preferred subclass of compounds of formula (I) are those wherein X is oxygen.

Another preferred subclass of compounds of formula (I) are those wherein Z is a glyoxylamide group.

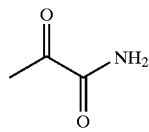

Most preferred are compounds of formula (I) wherein $R_3$ is the glyoxamide group. For the group $R_3$ it is preferred that the linking group —($L_3$)— be a bond.

IV. Preferred $R_4$ substituents:

Another preferred subclass of compounds of formula (I) are those wherein $R_4$ is a substituent having a linker with a linker length of 2 or 3 and the linker group, —($L_4$)—, for $R_4$ is selected from a group represented by the formula;

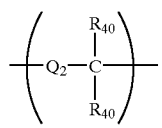

where $Q_2$ is selected from the group —($CH_2$)—, —O—, —NH—, —C(O)—, and —S—, and each $R_{40}$ is independently selected from hydrogen, $C_1-C_8$ alkyl, aryl, $C_1-C_8$ alkaryl, $C_1-C_8$ alkoxy, aralkyl, and halo. Most preferred are compounds where the linker, —($L_4$)—, for $R_4$ is selected from the specific groups;

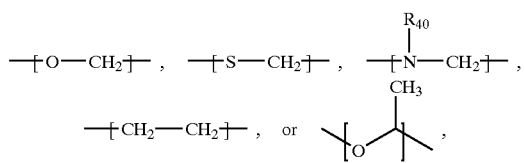

where $R_{40}$ is hydrogen or $C_1-C_8$ alkyl.

Preferred as the (acylsulfonamide group) in the group $R_4$ are acylsulfonamide groups selected from:

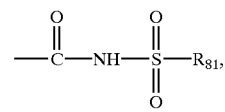

where $R_{81}$ is selected from —$CF_3$, $C_1-C_8$ alkyl, $C_1-C_8$ alkoxy, $C_1-C_8$ alkylthio, $C_1-C_8$ alkylamino, $C_1-C_8$ haloalkyl, $C_1-C_{14}$ aralkyl, $C_1-C_{14}$ alkylaryl, aryl, thioaryl, $C_3-C_{14}$ carbocyclic radical, $C_3-C_{14}$ heterocyclic radical. A salt or a solvate derivative of the (acylsulfonamide group) is also suitable.

Particularly preferred are acylsulfonamide groups selected from:

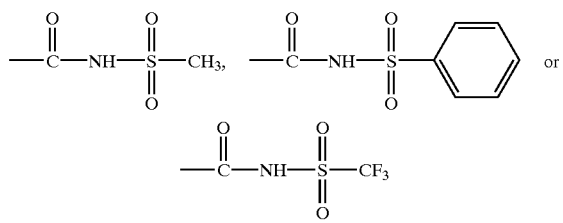

or salts or solvates thereof.

V. Preferred $R_5$ Substituents:

Preferred linker, —($L_a$)—, for $R_5$ is selected from the group consisting of;

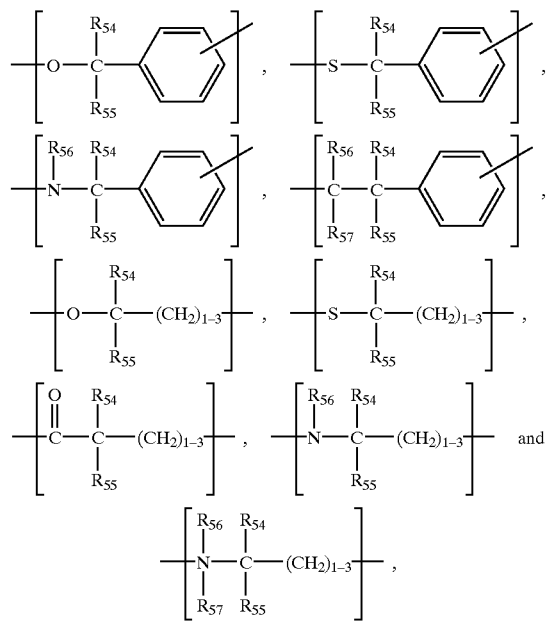

wherein $R_{54}$, $R_{55}$, $R_{56}$ and $R_{57}$ are each independently hydrogen, $C_1-C_8$ alkyl, $C_1-C_8$ haloalkyl, aryl, $C_1-C_8$ alkoxy, or halo.

VI. Preferred (acylsulfonamide group) for $R_4$ and/or $R_5$ substitutions:

At least one of $R_4$ and $R_5$ must be the group, —($L_a$)— (acylsulfonamide group). The preferred (acylsulfonamide group) on the group —($L_a$)—(acylsulfonamide group) of $R_4$ or $R_5$ is selected from

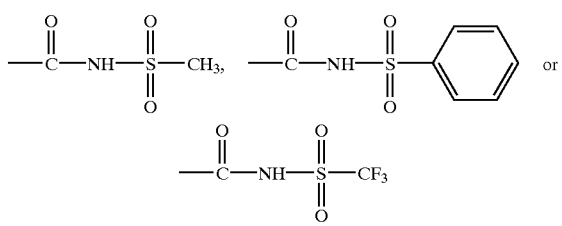

In addition, it is preferred that only one $R_4$ or $R_5$ substituents be the group, —($L_a$)—(acylsulfonamide group).

Most preferred is that the $R_4$ substituent be the group, —($L_a$)—(acylsulfonamide group).

V. Preferred $R_6$ substituents:

Another preferred subclass of compounds of formula (I) are those wherein for $R_6$ the non-interfering substituent is methyl, ethyl, propyl, isopropyl, —S—$CH_3$, —O—$CH_3$, $C_4$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where R is $C_1$–$C_8$ alkyl and n is from 1 to 8.

Preferred compounds of the invention are those having the general formula (II), or a pharmaceutically acceptable salt or solvate derivative thereof;

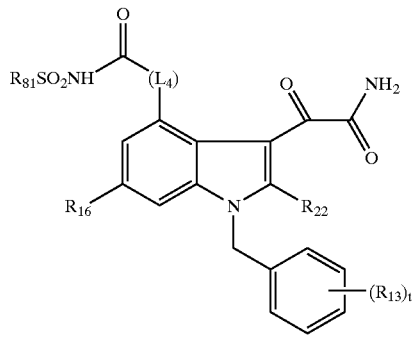

(II)

wherein;

$R_{81}$ is selected from $C_1$–$C_8$ alkyl, $C_1$–$C_8$ alkoxy, $C_1$–$C_8$ alkylthio $C_1$–$C_8$ haloalkyl, $C_1$–$C_8$ alkylamino, $C_1$–$C_{14}$ aralkyl, $C_1$–$C_{14}$ alkylaryl, aryl, thioaryl, $C_3$–$C_{14}$ carbocycle, $C_3$–$C_{14}$ heterocycle.

$R_{22}$ is selected from hydrogen, methyl, ethyl, propyl, isopropyl, cyclopropyl, —F, —$CF_3$, —Cl, —Br, or —O—$CH_3$;

—($L_4$)— is a divalent group selected from;

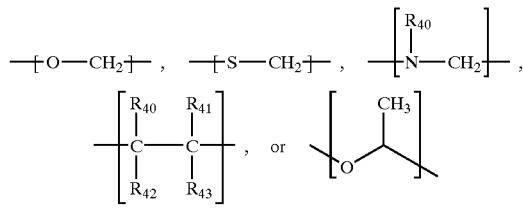

where $R_{40}$, $R_{41}$, $R_{42}$, and $R_{43}$ are each independently selected from hydrogen or $C_1$–$C_8$ alkyl.

$R_{16}$ is selected from hydrogen, $C_1$–$C_8$ alkyl, $C_1$–$C_8$ alkoxy, $C_1$–$C_8$ alkylthio $C_1$–$C_8$ haloalkyl, $C_1$–$C_8$ hydroxyalkyl, and halo.

$R_{13}$ is selected from hydrogen and $C_1$–$C_8$ alkyl, $C_1$–$C_8$ alkoxy, —S—($C_1$–$C_8$ alkyl), $C_1$–$C_8$ haloalkyl, $C_1$–$C_8$ hydroxyalkyl, and halo, and t is an integer from 0 to 5.

A preferred compound (and all pharmaceutically acceptable salts and solvate derivatives thereof) which is illustrative of the compounds of the invention is as follows:

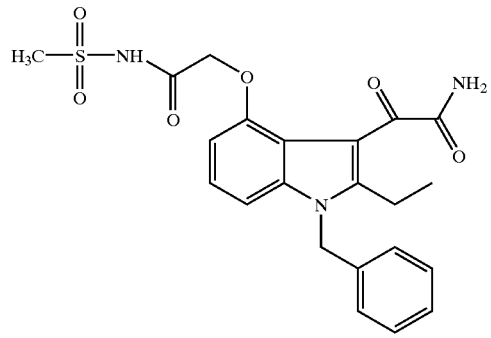

(C1)

The salts of the above indole compounds represented by formulae (I) and (II) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acylsulfonamide in solution with a base or by exposing the acylsulfonamide to an ion exchange resin. For example, the (acylsulfonamide group) of the substituent $R_4$ of Formula I may be selected as —(CO)NHSO$_2$CH$_3$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans- isomeric forms of the compounds. The R- and S- isomers and mixtures thereof, including racemic mixtures as well as mixtures of cis- and trans- isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of diastereomers and diastereomers, because they have different melting points, different boiling points, and different solubilities can be separated by conventional means, such as crystallization.

Method of Making the Compounds of the Invention:

The synthesis of the indole compound of the invention (viz., Compounds of Formulae I and II) can be accomplished by well known methods as recorded in the chemical literature. In particular, the indole starting materials may be prepared by the synthesis schemes taught in U.S. Pat. No. 5,654,326; the disclosure of which is incorporated herein by reference. Procedures useful for the synthesis of the starting material are shown in the Scheme below:

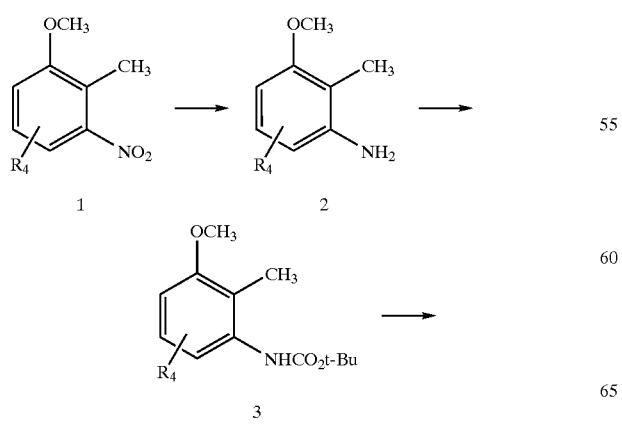

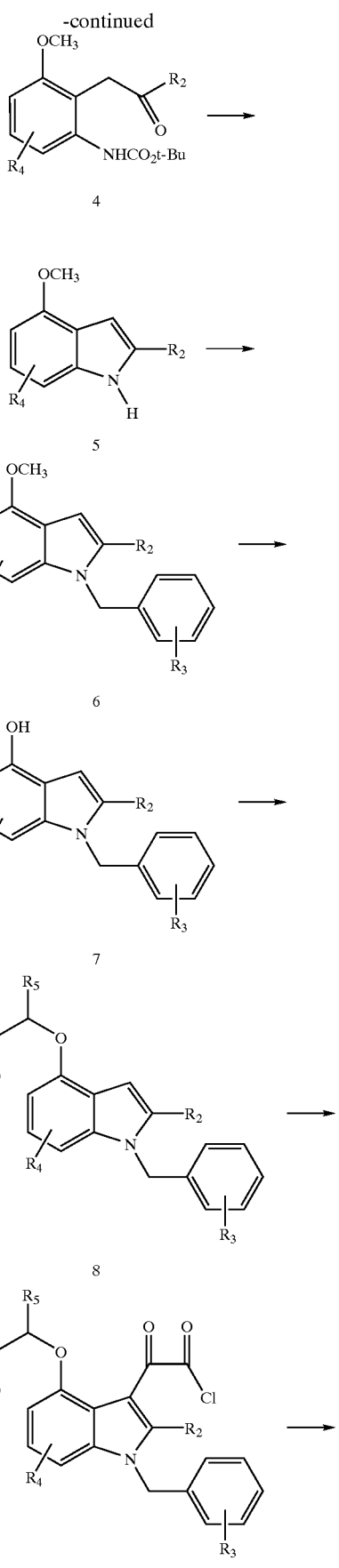

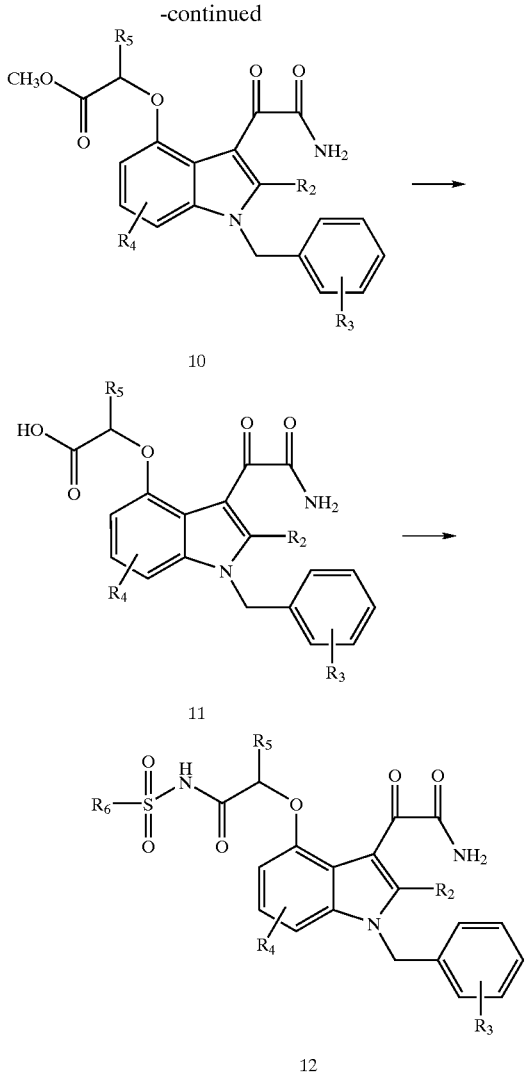

wherein, for the preceding Scheme, $R_6$ is an organic substituent or —$CF_3$, $R_4$ is equivalent to $R_6$ or $R_7$ in Formula I, $R_2$ is equivalent to $R_2$ in formula I, $R_3$ is equivalent to $(R_{12})_t$ in Formula I and $R_5$ is —H or $C_1$-$C_8$ alkyl.

To obtain the glyoxylamides substituted in the 4-position with an acidic function through an oxygen atom, the reactions outlined in scheme 1 are used (for conversions 1 thru 5, see ref. Robin D. Clark, Joseph M. Muchowski, Lawrence E. Fisher, Lee A. Flippin, David B. Repke, Michel Souchet, *Synthesis*, 1991, 871–878, the disclosures of which are incorporated herein by reference). The ortho-nitrotoluene, 1, is readily reduced to the 2-methylaniline, 2, using Pd/C as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butylcarbonyl derivative, 3, in good yield. The dilithium salt of the dianion of 3 is generated at −40 to −20° C. in THF using sec-butyl lithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, Adv. Drug Res., 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The α-[(indol-4-yl)oxy]alkanoic acid ester, 8, is reacted with oxalyl chloride in methylene chloride to give 9, which is not purified but reacted directly with ammonia to give the glyoxamide 10. This product is hydrolyzed using 1N sodium hydroxide in MeOH. The glyoxylamide, 11, is isolated either as the free carboxylic acid. Sulfonamide formation is accomplished by reaction of the appropriate sulfonamide with the indole acid (glyoxylamide) 11, in the presence of a suitable coupling agent such as EDCI (1-(3-dimethylaminopropyl)-3-ethylcarbodiimide hydrochloride) and dimethylaminopyridine as a base to afford the indole acylsulfonamide, 12. The formation of the sulfonamide, 12, can be accomplished by other procedures known in the art.

An alternative method of making starting materials substituted in the 4-position is described in provisional patent application No. 60/082110 filed Apr. 17, 1998 and entitled "PROCESS FOR PREPARING 4-SUBSTITUTED-1H-INDOLE-3-GLYOXYLAMIDES." The esters described therein may be hydrolyzed to the acid form suitable for a starting material for preparing compounds of the invention.

Methods of Using the Compounds of the Invention:

The method of the invention for inhibiting $sPLA_2$ mediated release of fatty acids comprises contacting mammalian $sPLA_2$ with an therapeutically effective amount of indole compounds corresponding to Formulae (I) or (II) as described herein including salt or a prodrug derivative thereof.

Another aspect of this invention is a method for treating Inflammatory Diseases such as inflammatory bowel disease, septic shock, adult respiratory distress syndrome, pancreatitis, trauma, bronchial asthma, allergic rhinitis, rheumatoid arthritis, osteoarthritis, and related diseases which comprises administering to a mammal (including a human) a therapeutically effective dose of the indole compound of the invention (see, formula I and II).

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention (per Formulae I or II) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the indole compound of the invention together with a pharmaceutically acceptable carrier or diluent therefor. The present pharmaceutical formulations are prepared by known procedures using well known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or (II) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| | |
|---|---:|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| | |
|---|---:|
| Active ingredient | 80 mg |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| | |
|---|---:|
| Active ingredient | 225 mg |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| | |
|---|---:|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---:|
| Active ingredient | 100 mg |
| Isotonic saline | 1,000 ml |

The solution of the above ingredients generally is administered intravenously to a subject at a rate of 1 ml per minute.

The compounds of the invention are prepared by the general procedure of reacting indole compound starting materials having carboxyl functionality at the 4- or 5-position with an $R_{81}$-sulfonamide, where $R_{81}$ is as described, supra.

All of the products of the Examples described below as well as intermediates used in the following procedures showed satisfactory nmr and ir spectra. They also had the correct elemental analyses values.

EXAMPLE A

This Example illustrates the preparation of a starting material for preparing the acylsulfonamide functional indole compounds of the invention (viz., formulae I and II).

Preparation of [[3-(2-amino-1,2-dioxoethyl)-2-ethyl-1-(phenylmethyl)-1H-indol-4-yl]oxy]acetic acid, a compound represented by the formula:

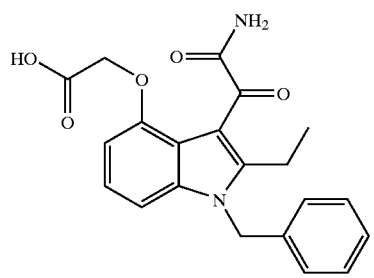

Part A. Preparation of 2-Ethyl-4-methoxy-1H-indole.

A solution of 140 mL (0.18 mol) of 1.3 M sec-butyl lithium in cyclohexane is added slowly to N-tert-butoxycarbonyl-3-methoxy-2-methylaniline (21.3 g, 0.09 mol) in 250 mL of THF keeping the temperature below −40° C. with a dry ice-ethanol bath. The bath is removed and the temperature allowed to rise to 0° C. and then the bath replaced. After the temperature is cooled to −60° C., 18.5 g (0.18 mol) of N-methoxy-N-methylpropanamide in an equal volume of THF is added dropwise. The reaction mixture is stirred 5 minutes, the cooling bath removed and stirred an additional 18 hours. It is then poured into a mixture of 300 mL of ether and 400 mL of 0.5N HCl. The organic layer is separated, washed with water, brine, dried over MgSO$_4$, and concentrated at reduced pressure to give 25.5 g of a crude of 1-[2-(tert-butoxycarbonylamino)-6-methoxyphenyl]-2-butanone. This material is dissolved in 250 mL of methylene chloride and 50 mL of trifluoroacetic acid and stirred for a total of 17 hours. The mixture is concentrated at reduced pressure and ethyl acetate and water added to the remaining oil. The ethyl acetate is separated, washed with brine, dried (MgSO$_4$) and concentrated. The residue is chromatographed three times on silica eluting with 20% EtOAc/hexane to give 13.9 g of 2-ethyl-4-methoxy-1H-indole.

Analyses for $C_{11}H_{13}NO$: Calculated: C, 75.40; H, 7.48; N, 7.99; Found: C, 74.41; H, 7.64; N, 7.97.

Part B. Preparation of 2-Ethyl-4-methoxy-1-(phenylmethyl)-1H-indole.

2-Ethyl-4-methoxy-1H-indole (4.2 g, 24 mmol) is dissolved in 30 mL of DMF and 960 mg (24 mmol) of 60% NaH/minerial oil is added. After 1.5 hours, 2.9 mL(24 mmol) of benzyl bromide is added. After 4 hours, the mixture is diluted with water and extracted twice with ethyl acetate. The combined ethyl acetate is washed with brine, dried (MgSO$_4$) and concentrated at reduced pressure. The residue is chromatographed on silica gel and eluted with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole.

3.1 g (11.7 mmol) of 2-ethyl-4-methoxy-1-(phenylmethyl)-1H-indole is O-demethylated by treating it with 48.6 mL of 1M BBr$_3$/CH$_2$Cl$_2$, then stirred at room temperature for 5 hours and concentrated at reduced pressure. The residue is dissolved in ethyl acetate, then washed with brine and dried. The reaction product is then chromatographed on silica gel (eluted with 20% EtOAc/hexane) to give 1.58 g (54% yield) of 2-ethyl-4-hydroxy-1-(phenylmethyl)-1H-indole, mp, 86–90° C.

Analyses for $C_{17}H_{17}NO$: Calculated: C, 81.24; H, 6.82; N, 5.57; Found: C, 81.08; H, 6.92; N, 5.41.

Part D. Preparation of [[2-Ethyl-1-(phenylmethyl)-1H-indol-4-yl]oxy]acetic acid methyl ester.

2-ethyl-4-hydroxy-1-(phenylmethyl)-1H-indole (1.56 g, 6.2 mmol) is treated with 248 mg (6.2 mmol) of 60% NaH/mineral oil in dimethylformamide and the mixture stirred for 0.67 hours. 0.6 mL(6.2 mmol) of methyl bromoacetate is added and the mixture stirred for 17 hours. The reaction mixture is diluted with water and 5 then extracted with ethyl acetate. The ethyl acetate solution is washed with brine, dried, and concentrated at reduced pressure. The product is purified by chromatography over silica gel eluting with 20% EtOAc/hexane, to give 1.37 g (69% yield) of [[2-ethyl-1-10 (phenylmethyl)-1H-indol-4-yl]oxy]acetic acid methyl ester, 89–92° C.

Analyses for $C_{20}H_{21}NO_3$: Calculated: C, 74.28; H, 6.55; N, 4.33; Found: C, 74.03; H, 6.49; N, 4.60.

Part E. Preparation of [[3-(2-Amino-1,2-dioxoethyl)-2-ethyl-1-(phenylmethyl)-1H-indol-4-yl]oxy]acetic acid methyl ester.

1.36 g (4.2 mmol) of [[2-ethyl-1-(phenylmethyl)-1H-indol-4-yl]oxy]acetic acid methyl ester is reacted first with 0.4 mL (4.2 mmol) of oxalyl chloride in methylene chloride and stirred for 1.5 hours. Anhydrous ammonia (in excess) is bubbled into the reaction mixture and the mixture is stirred for 1.5 hours and evaporated at reduced pressure to give a white solid. This is stirred with ethyl acetate and the insoluble material separated and dried to give 1.37 g of a mixture of ([[3-(2-amino-1,2-dioxoethyl)-2-ethyl-1-(phenylmethyl)-1H-indol-4-yl]oxy]acetic acid methyl ester and ammonium chloride. This mixture melted at 172–187° C.

Part F. Preparation of [[3-(2-Amino-1,2-dioxoethyl)-2-ethyl-1-(phenylmethyl)-1H-indol-4-yl]oxy]acetic acid.

A mixture of 788 mg (2 mmol) of [3-(2-amino-1,2-dioxoethyl)-2-ethyl-1-(phenylmethyl)-1H-indol-4-yl]oxy]acetic acid methyl ester, 10 mL of in NaOH and 30 mL of MeQH is heated to maintain relfux for 0.5 hour, stirred at room temperature for 0.5 hour and concentrated at reduced pressure. The residue is taken up in ethyl acetate and water, the aqueous layer separated and made acidic to pH 2–3 with 1N HCl. The precipitate is filtered and washed with ethyl acetate to give 559 mg (74% yield) of [[3-(2-amino-1,2-dioxoethyl)-2-ethyl-1-(phenylmethyl)-1H-indol-4-yl]oxy] acetic acid, mp, 230–234° C.

Analyses for $C_{21}H_{20}N_2O_5$: Calculated: C, 65.96; H, 5.80; N, 7.33; Found: C, 66.95; H, 5.55; N, 6.99.

General Reaction Scheme used in Examples 1 to 5:

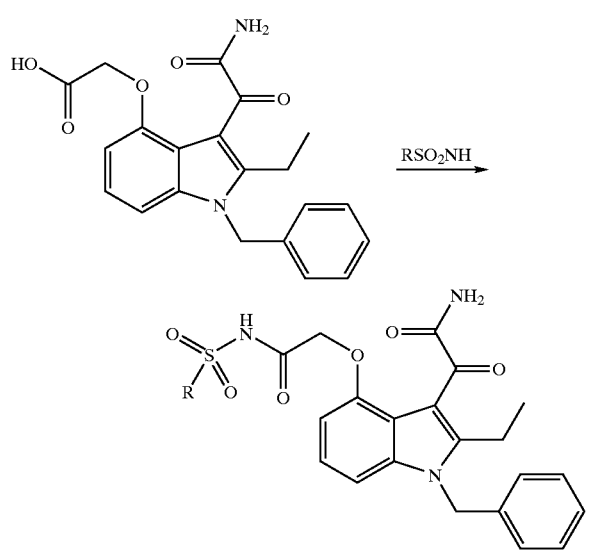

EXAMPLE 1

Preparation of 1-Benzyl-2-ethyl-4-methanesulfonamidoylmethyloxy-indole-3-glyoxylamide

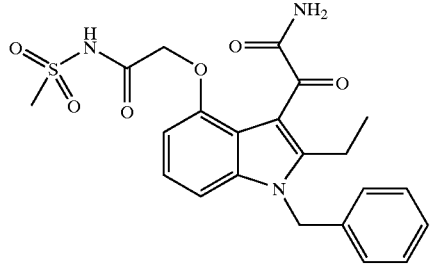

To 100 mg (0.26 mmol) of 1-benzyl-2-ethyl-4-carboxymethyloxy-indole-3-glyoxylamide suspended in 3.7 ml CH$_2$Cl$_2$ was added 4-dimethylaminopyridine (48 mg, 0.39 mmol), methanesulfonamide (50 mg, 0.52 mmol), and 1-(3-dimethylaminopropyl)-3-ethylcarbodiimide hydrochloride (50 mg, 0.26 mmol), respectively. After 23 h, the reaction was diluted with CH$_2$Cl$_2$ and extracted with 1 N HCl, then brine. The organic layer was dried with sodium sulfate and evaporated in vacuo. The residue was chromatographed on silica gel eluting with a CH$_2$Cl$_2$/MeOH gradient to give the titled product (22.2 mg, 19%).

MS (ES+) 458, 413

Elemental Analyses for C$_{22}$H$_{23}$N$_3$O$_6$S: Calculated: C 57.76; H 5.07; N 9.18 Found: C 57.66; H 5.27; N 8.92

EXAMPLE 2

Preparation of 1-Benzyl-2-ethyl-4-benzenesulfonamidoylmethyloxy-indole-3-glyoxylamide

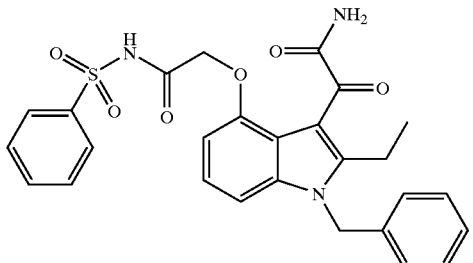

To 200 mg (0.53 mmol) of 1-benzyl-2-ethyl-4-carboxymethyloxy-indole-3-glyoxylamide suspended in 5.3 ml CH$_2$Cl$_2$ was added 4-dimethylaminopyridine (96 mg, 0.79 mmol), benzenesulfonamide (165 mg, 1.05 mmol), and 1-(3-dimethylaminopropyl)-3-ethylcarbodiimide hydrochloride (101 mg, 0.53 mmol), respectively. After 19 h, the reaction was diluted with CH$_2$Cl$_2$ and extracted with 1 N HCl, then brine. The organic layer was dried with sodium sulfate and evaporated in vacuo. The residue was chromatographed on silica gel eluting with a CH$_2$Cl$_2$/MeOH gradient to give impure product. Recrystallation from acetone/hexane provided the titled product (62 mg, 23%). MS (ES+) 520, 475

Elemental Analyses for C$_{27}$H$_{25}$N$_3$O$_6$S: Calculated: C 62.42; H 4.85; N 8.09 Found: C 62.64; H 4.97; N 8.31

EXAMPLE 3

Preparation of 1-Benzyl-2-ethyl-4-trifluoromethanesulfonamidoylmethyloxy-indole-3-glyoxylamide

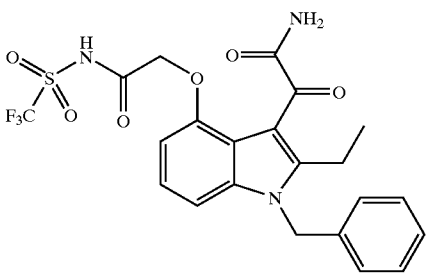

To 200mg (0.53 mmol) of 1-benzyl-2-ethyl-4-carboxymethyloxy-indole-3-glyoxylamide suspended in 5.3ml CH$_2$Cl$_2$ was added 4-dimethylaminopyridine (96 mg, 0.79 mmol), trifluoromethanesulfonamide (157 mg, 1.05 mmol), and 1-(3-dimethylaminopropyl)-3-ethylcarbodiimide hydrochloride (101 mg, 0.53 mmol), respectively. After 24 h, the reaction was diluted with CH$_2$C$_{12}$ and extracted with 1 N HCl, then brine. The organic layer was dried with sodium sulfate and evaporated in vacuo. The residue was chromatographed on silica gel eluting with a CH$_2$Cl$_2$/MeOH gradient to give impure product. Recrystallation from acetone/hexane provided the titled product (89 mg, 33%).

MS (ES+) 512, 467; MS (Exact); Calculated: 512.1103; Found: 512.1108;

Elemental Analyses for C$_{22}$H$_{20}$F$_3$N$_3$O$_6$S: Calculated: C 51.66; H 3.94; N 8.22; Found: C 49.68; H 3.78; N 7.86.

EXAMPLE 4

Preparation of 1-Benzyl-2-ethyl-4-(2-methylbenzenesulfonamidoylmethyloxy)-indole-3-glyoxylamide

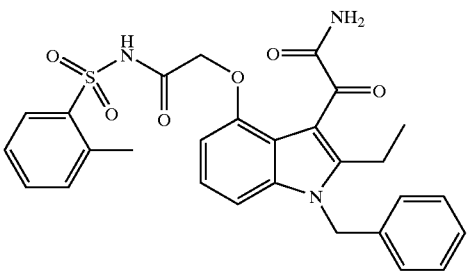

To 200 mg (0.53 mmol) of 1-benzyl-2-ethyl-4-10carboxymethyloxy-indole-3-glyoxylamide suspended in 5.3ml CH$_2$Cl$_2$ was added 4-dimethylaminopyridine (96 mg, 0.79 mmol), 2-methylbenzenesulfonamide (180 mg, 1.05mmol), and 1-(3-dimethylaminopropyl)-3-ethylcarbodiimide hydrochloride (101 mg, 0.53 mmol) , respectively. After 23 h, the reaction was diluted with CH$_2$Cl$_2$ and extracted with 1 N HCl, then brine. The organic layer was dried with sodium sulfate and evaporated in vacuo. The residue was chromatographed on silica gel eluting with a CH$_2$Cl$_2$/MeOH gradient to give impure product. Recrystallation from acetone/hexane provided the titled product (102 mg, 36%).

MS (ES+) 534, 489;

MS (Exact); Calculated: 534.1699; Found: 534.1696;

Elemental Analyses for $C_{28}H_{27}N_3O_6S$: Calculated: C 63.03; H 5.10; N 7.87; Found: C 63.30; H 5.87; N 7.70.

EXAMPLE 5

Preparation of 1-Benzyl-2-ethyl-4-(4-(2-aminoethyl) benzenesulfonamidoylmethyloxy)-indole-3-glyoxylamide, Hydrochloride Salt

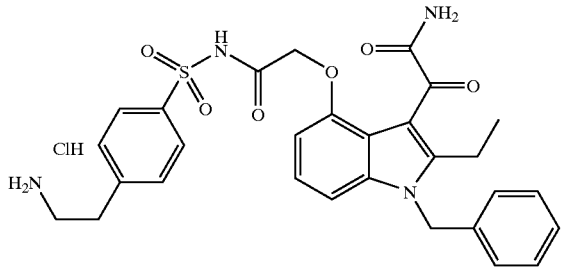

Part A. 4-(2-t-Butoxycarbonylamino) ethylbenzenesulfonamide

To 2.00 g (10.0 mmol) of 4-(2-aminoethyl) benzenesulfonamide suspended in a mixture of 10 ml THF, 10 ml $CH_2Cl_2$, and 3 ml DMF was added di-t-butyldicarbonate (2.20 g, 10.0 mmol) After 19 h, the reaction was diluted with EtOAc and extracted with 1 N HCl, then with brine. The organic layer was dried with sodium sulfate and evaporated in vacuo. The residue was triturated with hexanes and filtered to give the subtitled product (1.85 g, 62%).

Part B. 1-benzyl-2-ethyl-4-(4-(2-t-butoxycarbonylaminoethyl) benzenesulfonamidoylmethyloxy)-indole-3-glyoxylamide

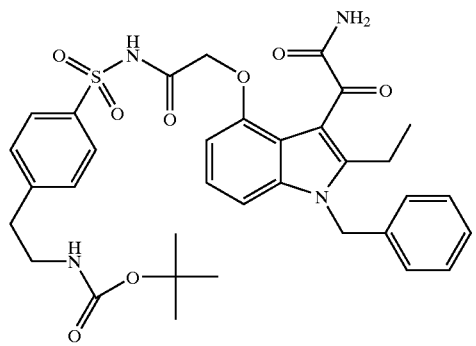

To 275 mg (0.72 mmol) of 1-benzyl-2-ethyl-4-carboxymethyloxy-indole-3-glyoxylamide and 0.38ml (2.17 mmol) N-diisopropyl, N-ethylamine suspended in 4.8 ml $CH_2Cl_2$ was added 4-dimethylaminopyridine (59 mg, 0.48 mmol), 4-(2-t-butoxycarbonylamino) ethylbenzenesulfonamide (145 mg, 0.48mmol), and 1-(3-dimethylaminopropyl)-3-ethylcarbodiimide hydrochloride (0.21 g, 1.09 mmol), respectively. After 24 h, the reaction was diluted with $CH_2Cl_2$ and extracted with 1 N HCl, then with brine. The organic layer was dried with sodium sulfate and evaporated in vacuo. The residue was chromatographed on silica gel eluting with a hexane/acetone gradient, then with 10:1 $CH_2Cl_2$/MeOH to give the subtitled product (248 mg, 78%).

MS (ES+) 563, (ES−) 661; Elemental Analyses for $C_{34}H_{38}N_4O_8S$: Calculated: C 61.62; H 5.78; N 8.45; Found: C 59.42; H 5.91; N 7.10;

Part C. 1-benzyl-2-ethyl-4-(4-(2-aminoethyl) benzenesulfonamidoylmethyloxy)-indole-3-glyoxylamide, hydrochloride salt

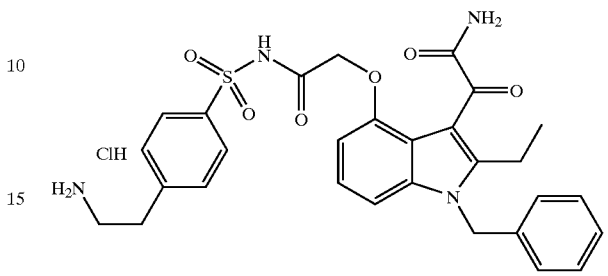

To 115 mg (0.17mmol) of 1-benzyl-2-ethyl-4-(4-(2-t-butoxycarbonylaminoethyl) benzenesulfonamidoylmethyloxy)-indole-3-glyoxylamide suspended in 8.7 ml $CH_2Cl_2$ was added trifluoroacetic acid (4.32 ml, 56 mmol). After 2 h, the reaction was evaporated in vacuo. The residue was triturated with 5:1 $CH_2Cl_2$/EtOAc, filtered, and chromatographed on reverse phase silica gel eluting with an acetonitrile/water/HCl gradient to give the titled product (56 mg, 54%).

MS (ES+) 563, (ES−) 561; Elemental Analyses for $C_{29}H_{31}ClN_4O_6S$: Calculated: C 58.14; H 5.22; N 9.35; Found: C 57.07; H 5.02; N 9.12.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference): Reagents:

REACTION BUFFER—

| | |
|---|---|
| CaCl2.2H2O | (1.47 g/L) |
| KCl | (7.455 g/L) |
| Bovine Serum Albumin (fatty acid free) (Sigma A-7030, product of Sigma Chemical Co., St. Louis MO, USA) | (1 g/L) |
| TRIS HCl | (3.94 g/L) |
| pH 7.5 (adjust with NaOH) | |

ENZYME BUFFER—

0.05 NaOAc.3H20, pH 4.5

0.2 NaCl

Adjust pH to 4.5 with acetic acid DTNB—5,5'-dithiobis-2-nitrobenzoic acid

RACEMIC DIHEPTANOYL THIO—PC racemic 1,2-bis (heptanoylthio)-1,2-dideoxy-sn-glycero-3-phosphorylcholine TRITON X-100™ prepare at 6.249 mg/ml in reaction buffer to equal 10 uM. REACTION MIXTURE—

A measured volume of racemic diheptanoyl thio PC supplied in chloroform at a concentration of 100 mg/ml is taken to dryness and redissolved in 10 millimolar TRITON X-101™ nonionic detergent aqueous solution. Reaction Buffer is added to the solution, then DTNB to give the Reaction Mixture.

The reaction mixture thus obtained contains 1mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ were determined by plotting log concentration versus inhibition values in the range from 10–90% inhibition.

Results of Human Secreted Phospholipase A$_2$ Inhibition Tests

TABLE

| Compound of Example No. | Inhibition of human secreted PLA$_2$ IC50 ± mean deviation |
|---|---|
| 1 | 12 nM |
| 2 | 7 nM |
| 3 | 17 nM |
| 4 | 9 nM |
| 5 | 16 nM |

The compounds of Example 1 to 5 are useful in inhibiting sPLA$_2$.

While the present invention has been illustrated above by certain specific embodiments, it is not intended that these specific examples should limit the scope of the invention as described in the appended claims. WO 00107591 PCTIUS99/17460

We claim:
1. An indole compound represented by the formula (I), or a pharmaceutically acceptable salt, or solvate derivative thereof;

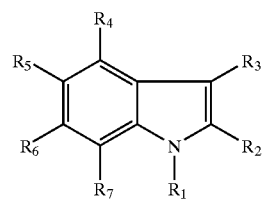

wherein;

R$_1$ is the group —(L$_1$)—R$_{11}$, where, —(L$_1$)— is —(CH$_2$)— and R$_{11}$ is C$_7$-C$_{20}$ alkyl, C$_7$-C$_{20}$ haloalkyl, C$_7$-C$_{20}$ alkenyl, C$_7$-C$_{20}$ alkynyl, or a carbocyclic radical;

R$_2$ is —CH$_3$ or C$_2$H$_5$;

R$_3$ is —C(O)—C(O)—NH$_2$; R$_4$ is the group —(L$_a$)-(acylsulfonamide group) where —(L$_a$)— is —O—CH$_2$— and the acylsulfonamide group is —C(O)—CH—S(O)(O)—R$_{81}$ and R$_{81}$ is —CF$_3$, CH$_3$ or C$_2$H$_5$;

R$_5$ is hydrogen; and

R$_6$ and R$_7$ are hydrogen, or a carbocyclic radical.

2. A pharmaceutical formulation comprising a indole compound as claimed in claim 1 together with a pharmaceutically acceptable carrier or diluent therefor.

3. A method of inhibiting sPLA$_2$ mediated release of fatty acid which comprises contacting sPLA$_2$ with an therapeutically effective amount of indole compound as claimed in claim 1.

4. A method of treating a mammal, including a human, to alleviate the pathological effects of Inflammatory Diseases; wherein the method comprises administration to said mammal of at least one indole compound as claimed in claim 1 in a pharmaceutically effective amount.

5. A indole compound represented by the formula.

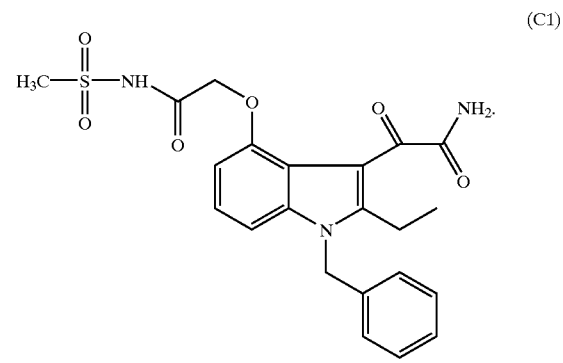

6. An indole compound selected from the group consisting of:
1-benzyl-2-ethyl-4-methanesulfonamidoylmethyloxy-indole-3-glyoxylamide; and
1-benzyl-2-ethyl-4-trifluoromethanesulfonamidoylmethyloxy-indole-3-glyoxylamide.

* * * * *